United States Patent [19]

Schaaf et al.

[11] 4,232,173

[45] Nov. 4, 1980

[54] 15-SULFONAMIDOPROSTAGLANDIN DERIVATIVES

[75] Inventors: Thomas K. Schaaf, Old Lyme; James F. Eggler, Stonington, both of Conn.

[73] Assignee: Pfizer Inc., New York, N.Y.

[21] Appl. No.: 76,520

[22] Filed: Sep. 17, 1979

[51] Int. Cl.³ .......................................... C07C 177/00
[52] U.S. Cl. .................................. 562/430; 560/12; 260/340.9 P; 424/317; 424/321; 424/269; 424/279; 548/253; 564/98
[58] Field of Search ................ 560/12, 121; 562/430; 260/308 D, 340.9 P, 556 A; 424/317, 321, 269

[56] References Cited

U.S. PATENT DOCUMENTS

| | | | |
|---|---|---|---|
| 4,033,996 | 7/1977 | Cragoe et al. | 560/121 |
| 4,128,720 | 12/1978 | Hayashi et al. | 560/9 |

OTHER PUBLICATIONS

Derwent Abstract, 23210x/13, J5 1016–645, (10/2/76).

Primary Examiner—Paul J. Killos
Attorney, Agent, or Firm—Francis X. Murphy; Charles J. Knuth; Albin J. Nelson

[57] ABSTRACT

Synthetic prostaglandin E compounds having carboxylic acid, ester, tetrazol, sulfonamide or imide substitutions at C-1, a methanesulfonamido group replacing the C-15 hydroxy and an aryloxy group at C-16 are disclosed. They exhibit antisecretory biological activity.

7 Claims, No Drawings

15-SULFONAMIDOPROSTAGLANDIN DERIVATIVES

BACKGROUND

The prostaglandins are C-20 unsaturated fatty acids which exhibit diverse physiological effects. Their structure, nomenclature, biological activities and medicinal use have been described in U.S. Pat. No. 3,971,825 and U.S. Pat. No. 3,984,400.

A common problem confronting medical scientists who attempt to make biologically efficacious, synthetic drugs is modulation of the biological action of an appropriate lead compound. A traditional approach seeks an increase in biological potency. The prostaglandin approach, however, is framed around increased oral activity and increased duration of action. In addition, enhancement of one of the diverse physiological effects of the prostaglandin class and diminution of the others are sought so that the synthetic prostaglandins will not exhibit incompatible side effects. For example, it would be clinically inadvisable to administer an antiulcer synthetic prostaglandin that also causes diarrhea.

To achieve increased selectivity, researchers have concentrated their efforts on the "active" sites of the natural prostaglandins. In the main, these include the C-1 carboxylic acid group, the carboxylic acid side chain, the cyclopentane ring and the lipophilic end of the bottom side chain. Such work is publicized in the following patents: U.S. Pat. No. 4,024,179, U.S. Pat. No. 3,954,741, U.S. Pat. No. 3,987,087, U.S. Pat. No. 3,932,389, U.S. Pat. No. 3,054,741 and Netherlands Octooraanvrage No. 7,306,030.

SUMMARY

A class of C-15-sulfonamidoprostaglandin derivatives have been synthesized and found to have potent, gastric antisecretory activity and diminished smooth muscle activity. The class has generic formula I,

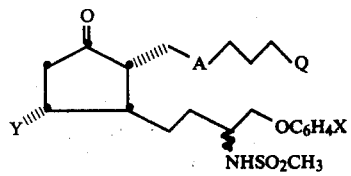

wherein Q is —$CO_2H$, $CO_2R$, tetrazol-5-yl, —$CONHSO_2R$ or —CONHCOR; A is ethylene or cis-vinylene; Y is OH or H; X is H, F, Cl, Br, $OCH_3$, $CF_3$ or $CH_3$; R is alkyl of 1 to 4 carbons or phenyl and the wavy line (∿) indicates the alpha or beta configuration.

The preferred embodiments include 9-oxo-11 alpha-hydroxy-15-methanesulfonamido-16-phenoxy-cis-5-omega-tetranorprostenoic acid of formula I wherein Q is $CO_2H$, A is cis-vinylene, Y is OH and X is H;
N-methanesulfonyl 9-oxo-11 alpha-hydroxy-15-methanesulfonamido-16-phenoxy-cis-5-omega-tetranorprostenamide of formula I wherein Q is $CONHSO_2CH_3$, A is cis-vinylene, Y is OH and X is H;
2-descarboxy-2-(tetrazol-5-yl)-9-oxo-11 alpha-hydroxy-15-methanesulfonamido-16-phenoxy-cis-5-omega-tetranorprostenoic acid of formula I wherein Q is tetrazol-5-yl, A is cis-vinylene, Y is OH and X is H.

The invention also includes pharmaceutical preparations containing pharmaceutical carriers and a derivative of formula I and a method of treating peptic ulcers by administering an efficacious amount of a derivative of formula I to a patient in need of such treatment.

DETAILED DESCRIPTION

The C-15 sulfonamido prostaglandin derivatives may be synthesized using a modification of the well known "Corey" prostaglandin synthesis. This synthesis is illustrated in Schemes A and B below which utilize the known, key intermediate 2-[(3 alpha-(p-phenylbenzoyloxy or hydrogen)-5 alpha-hydroxy-2 beta-formyl-cyclopent-1alpha-yl]acetic acid, gamma-lactone and conventional reactions to attach the bottom and top side chains.

SCHEME A

Bottom Side Chain Sequence

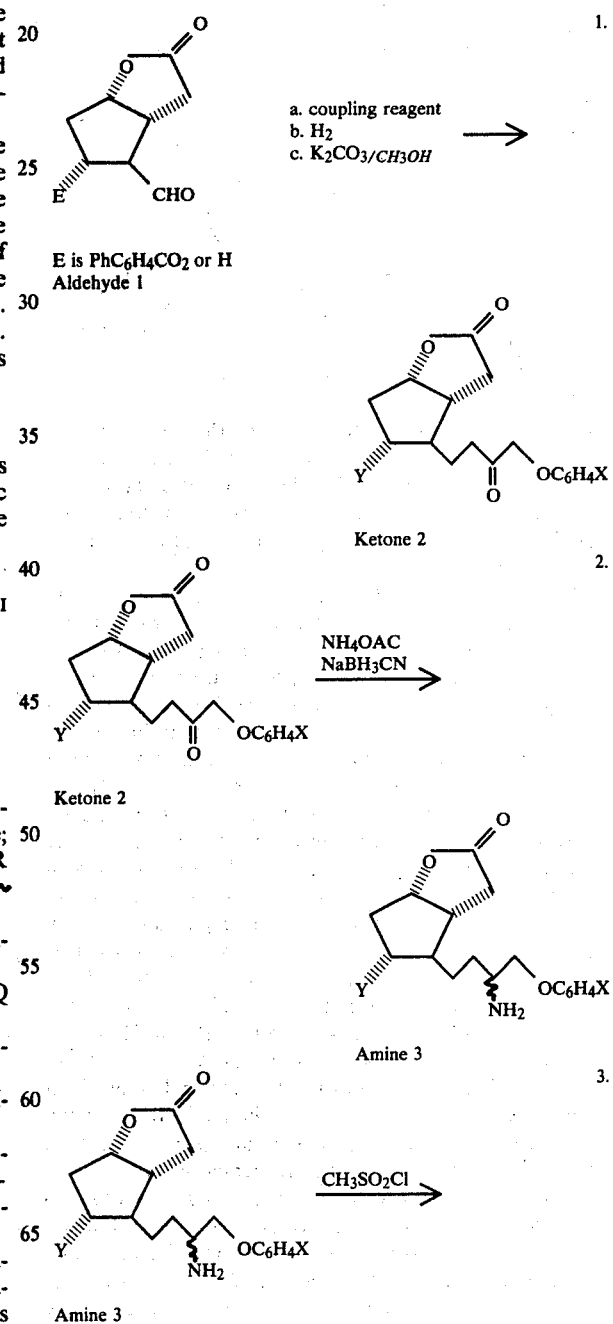

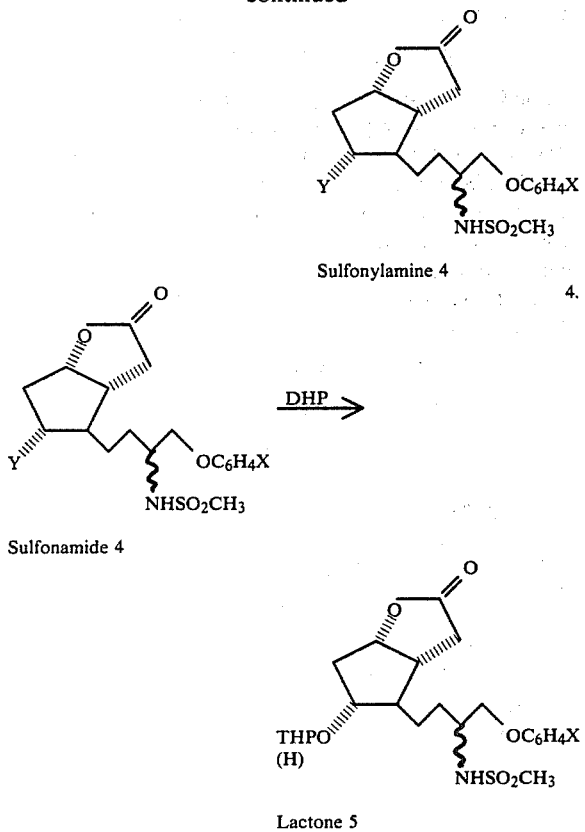

Sulfonylamine 4

Sulfonamide 4

Lactone 5

Scheme A presents the sequence for the attachment of the bottom side chain to the key intermediate, Aldehyde 1. The four reactions outline this procedure and except for reactions 2 and 3 which depict the attachment of the C-15 sulfonamido group, follow the "Corey" synthetic procedure.

Reaction 1 constitutes a coupling of the bottom side chain precursor Coupling Reagent to Aldehyde 1 and involves a series of steps. Step 1a is a "Wadsworth-Emmons" reaction of Aldehyde 1 and the Coupling Reagent which is dimethyl(2-oxo-3-aryloxypropyl)-phosphonoate. The sodium or lithium salt of the reagent is prepared by its reaction with a base such as sodium hydride or n-butyl lithium in a solvent such as tetrahydrofuran or dimethoxyethane. Aldehyde 1 is then added to this sodium or lithium salt at about 0° to 30° C. The coupling product Enone 1a 2-[3 alpha-(p-phenylbenzoyloxy or hydrogen)-5 alpha-hyroxy-2 beta-(3'-oxo-4'-aryloxybut-1-enyl)cyclopent-1 alpha-yl] acetic acid, gamma-lactone (not shown) is then purified using conventional techniques such as extraction, recrystallization, column chromatography or high pressure liquid chromatography. Ketone 2 is prepared from Enone 1a by hydrogenation in an inert polar organic solvent and over a noble metal catalyst (step 1b) and when E is $PhC_6H_4CO_2$, cleaving the paraphenyl benzoyl group using potassium carbonate in methanol (step 1c). Ketone 2 is purified using conventional techniques.

Reaction 2 illustrates the preparation of Amine 3 from Ketone 2. This reductive amination is conducted by reacting the Ketone with ammonium acetate and sodium cyanoborohydride in an alchol such as methanol, ethanol or isopropanol. After the excess cyanoborohydride is neutralized, Amine 3 is isolated and purified using conventional techniques.

Reaction 3 illustrates the sulfonylation of Amine 3 to produce sulfonylamine 4. Methanesulfonyl chloride is added to a solution of Amine 3 in an inert, organic solvent such as methylene chloride or ether which has been cooled to −78° C. After the reaction is substantially complete, sulfonylamine 4 is purified using conventional techniques.

Reaction 4 illustrates the conversion of sulfonylamine 4 to lactone 5 by addition of a tetrahydropyranyl group to the alcohol function and is used when Y is OH. When Y is H, the sulfonylamine 4 is the same as lactone 5. Sulfonylamine 4, dihydropyran and p-toluenesulfonic acid in an inert organic solvent such as methylene chloride or ether are reacted until the tetrahydropyranyl group formation is substantially complete. After extraction of the p-toluenesulfonic acid and removal of solvent, lactone 5 is used in the top side chain sequence, Scheme B, without further purification.

Scheme B illustrates the reactions whereby the top side chain is attached to lactone 5. It follows the "Corey" prostaglandin synthetic method.

SCHEME B

Top Side Chain Sequence

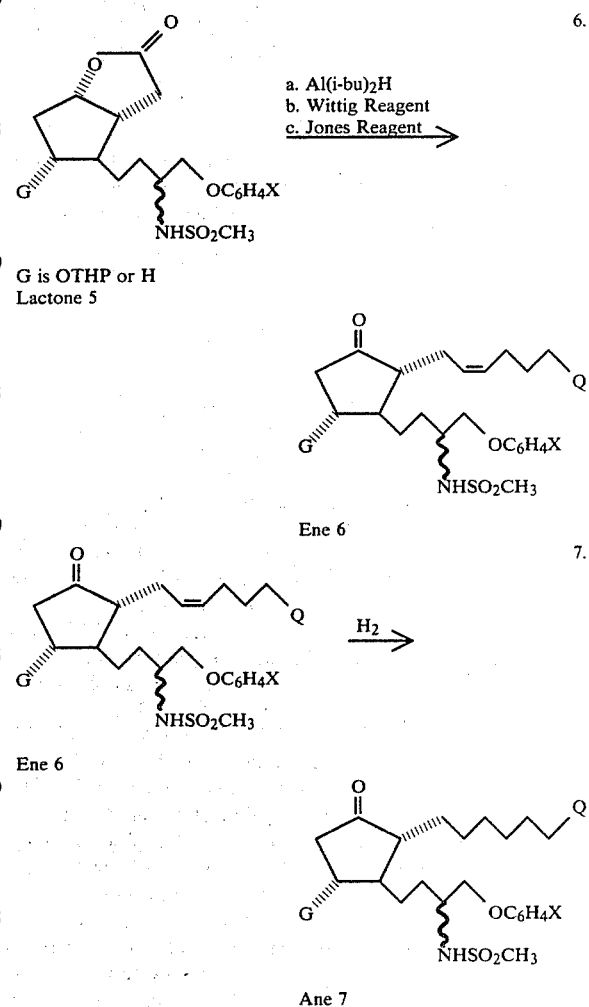

G is OTHP or H
Lactone 5

Ene 6

Ene 6

Ane 7

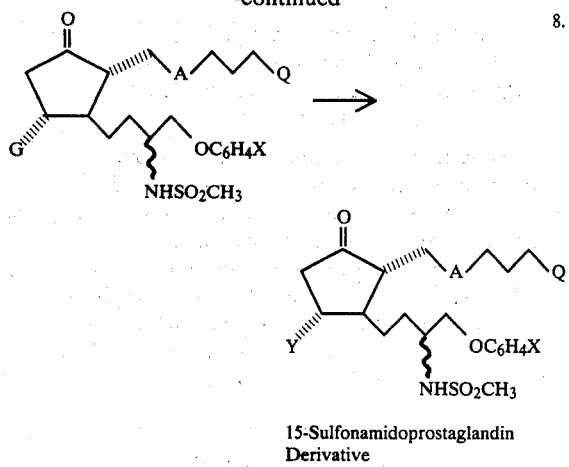

15-Sulfonamidoprostaglandin
Derivative

Reaction 6 constitutes the coupling of the top side chain precursor Wittig Reagent with Lactone 5 and covers three steps. Step 6a is the reduction of the lactone function of Lactone 5 to a hemiacetal function. Diisobutyl aluminum hydride and Lactone 5 are reacted in toluene at about −78° C. for about one hour. The reaction is then quenched with alcohol. The solvent is removed in vacuo and the residue partitioned between ether and 50% aqueous sodium potassium tartrate. Further purification using conventional techniques produces 2-[5 alpha-hydroxy-3 alpha-(tetrahydropyran-2-yloxy or hydrogen)-2 beta-3-methanesulfonamido-4-aryloxybut-1-yl)cyclopent-1 alpha-yl]acetaldehyde, gamma-hemiacetal,-Hemiacetal 6a (not shown).

Step 6b is the Wittig reaction of Hemiacetal 6a with the Wittig Reagent [4-(Q substituent)-n-butyl]triphenyl phosphonium bromide wherein Q is other than $CO_2R$. The ylide of Wittig Reagent is made in situ by reacting the Wittig Reagent with sodium methylsulfinylmethide in dimethyl sulfoxide. Hemiacetal 6a is then added to the ylide of the Wittig Reagent and the reaction is allowed to proceed until substantially complete. Purification using conventional techniques produces the Wittig product 6b (not shown). If it is desired to have Q as $CO_2R$, Wittig product 6b or the 15-sulfonamidoprostaglandin derivative wherein Q is $CO_2H$ may be esterified to produce Q as $CO_2R$ the acid is dissolved in a minimal amount of their and a stoichiometric amount of diazoalkane of 1 to 4 carbons or diphenyl sulfate is added. The ester is then isolated and purified using conventional techniques.

Step 6c is the oxidation of the 9-hydroxy group of Wittig product 6b to a ketone group using Jones reagent (chromic acid in sulfuric acid). The Jones reagent is added to a solution of Wittig product 6b in acetone at 0° C. After about five minutes the reaction is quenched with isopropyl alcohol. Purification using conventional techniques produces Ene 6.

Reaction 7 is the optional reduction of the C-5, C-6 double bond of Ene 6 to a single bond. Hydrogenation of Ene 6 over a noble metal catalyst in a solvent such as methanol or ethyl acetate at about 20° C. until one equivalent of hydrogen is absorbed produces Ane 7. It may be purified using conventional techniques.

Reaction 8 is the removal of the 11-hydroxy protecting group from Ene 6 or Ane 7 which is required when G is OTHP. When G is H, Ene 6 and Ane 7 together constitute the Derivative depicted in reaction 8 wherein Y is H. Stirring a solution of Ene 6 or Ane 7 in 65:35 acetic acid and water will cleave the THP group. After the reaction is substantially complete, purification using conventional techniques will provide the 15-sulfonamido prostaglandin derivative wherein Y is OH.

In numerous in vivo and in vitro tests, it can be shown that the 15-sulfonamidoprostaglandin derivatives exhibit extreme selectivity. Their biological achievement is the diminution of many of the physiological activities of the natural prostaglandins while maintaining activity in one area. The tests which allow such determination of selectivity include among others, a test for effect on isolated smooth muscle from guinea pig uterus, effect on dog blood pressure, inhibition of histamine induced bronchoconstriction in the guinea pig, inhibition of cold, stress-induced ulceration in the rat, antisecretory activity in the dog and diarrheal effect in the mouse.

After comparison with the responses caused by natural prostaglandin in the same tests, the physiological responses caused by the derivatives in these tests are helpful in determining their usefulness for the treatment of natural and pathological malconditions. Based upon such comparison, the 15-sulfonamidoprostaglandin derivatives have utility as selective antiulcer agents.

The results of biological tests of 9-oxo-11 alphahydroxy-15-methanesulfonamdo-16-phenoxy-cis-5-omegatetranorprostenoic acid show that it causes substantial inhibition of gastric acid secretion in the pentagastrin stimulated dog but causes significantly reduced smooth muscle responses in the guinea pig uterine strip test and the guinea pig bronchodilator test relative to $PGE_2$. The procedures for these standard biological tests are given below.

The derivatives can be used in a variety of pharmaceutical preparations which contain the derivative, or its pharmacologically acceptable salt. They may be administered in the same manner as natural prostaglandins by a variety of appropriate routes, such as intravenous, intraperitoneal and oral among others.

For pharmaceutical preparations and for solid compounding of the acid, tetrazole and sulfonimide derivatives the useful, pharmacologically acceptable salts are those with pharmacologically acceptable metal cations, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, benzylamine, alphaphenylethylamine, beta-phenylethylamine, as well as heterocyclic amines, e.g., piperidine, morpholine, pyrrolidine, and piperazine as well as amines containing water-solubilizing or hydrophilic groups, e.g., mono-, di-, and tri-ethanolamine, ethyldiethanolamine, galactamine, N-methylglucosamine, ephedrine phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The derivatives can be used in a variety of pharmaceutical preparations and they may be administered by several routes as described above. Although the particular dose, formulation and route of administration are dependent upon each patient's unique condition and the judgment of his attending physician, the guidelines below present the general treatment regimen.

The derivatives are useful as antiulcer agents. For treatment of peptic ulcers, these drugs are appropriately administered orally in the form of aqueous suspensions, ethanolic solutions or preferably in the form of capsules or tablets containing 0.001 to 0.10 mg/kg of derivative per dose with up to 12 doses per day or may be administered intravenously or intraperitoneally in the form of ethanolic or isotonic sterile solutions containing 0.5 to 50 micrograms of derivative per dose.

To prepare any of the above dosage forms or any of the numerous other forms possible, various inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical preparations may contain auxiliary material such as preserving agents, wetting agents, stabilizing agents, or other therapeutic agents such as antibiotics.

The following examples are merely illustrative, and in no way limit the scope of the appended claims.

In general, the temperatures of the reactions described in the examples, when unspecified, will be taken to mean ambient or room temperature which varies from 15° to 30° C.

The time requirements of the reactions described in the examples, unless otherwise stated, are determined by monitoring with thin layer chromatography (TLC). The usual TLC system is silica-gel on glass (E. Merck-Silica Gel plates, E. Merck, Dormstadt, W. Germany) with benzene/ether or methanol/chloroform as diluents and vanillin/ethanol or iodine as developers. ["Introduction to Chromatography" J. M. Bobbitt, A. E. Schwarting, R. J. Gritter, Van Norstrand-Renhold, N.Y. 1968]. As a general rule, the reaction in question is deemed essentially complete when the TLC spot representing the critical starting material disappears.

EXAMPLE 1

2-[3 alpha-p-phenylbenzoyloxy-5 alpha-hydroxy-2 beta-(3-oxo-4-phenoxy-trans-1-buten-1-yl)cyclopent-1 alpha-yl]acetic acid, gamma-lactone (Coupling Product 11a)

To a stirred suspension of 57% sodium hydride in mineral oil (1.3 g, 30.9 mmol) in tetrahydrofuran (THF) was added dropwise a solution of dimethyl (2-oxo-3-phenoxypropyl)phosphonate (coupling reagent) (8.4 g, 32.5 mmol) in THF. The mixture was stirred under nitrogen for 90 minutes then a solution of 2-[3 alpha-p-phenylbenzoyloxy-5 alpha-hydroxy-2 beta-formylcyclopent-1 alpha-yl]acetic acid, gamma-lactone (9.5 g, 27.1 mmol) in THF was added. After being stirred for 30 minutes, the reaction was quenched with acetic acid and concentrated. The residue was diluted with ethyl acetate, washed with water and brine, dried (MgSO$_4$) and concentrated. Purification of the crude product by column chromatography using mixtures of ethyl acetate in benzene as eluents provided 9.5 g (72%) of the above titled Coupling Product (11a) as a white solid, mp 124°–125° C. after trituration with ether:IR (KBr) 1775, 1715, 1675, 1630, cm$^{-1}$ (carbonyl groups) and 970 cm$^{-1}$ (trans CH=CH).

EXAMPLE 2

2-[3 alpha-p-phenylbenzoyloxy-5 alpha-hydroxy-2 beta-(3-oxo-4-phenoxybut-1-yl)cyclopent-1 alpha-yl]acetic acid, gamma lactone (Reduction Product 21b)

A heterogeneous mixture of the Coupling Product (11a) of Example 1 (5.74 g, 11.9 mmol) and 5% palladium on carbon (200 mg) in ethyl acetate (30 ml) and methanol (20 ml) was treated with 50 lbs of hydrogen in a Parr Shaker until hydrogen consumption ceased. The catalyst was collected by filtration and the filtrate concentrated to provide 5.71 g, (99%) of the above titled Reduction Product (21b) as a viscous, colorless oil which was used without further purification.

EXAMPLE 3

2-[3 alpha,5 alpha-dihydroxy-2 beta-(3-oxo-4-phenoxybut-1-yl)cyclopent-1 alpha-yl]acetic acid, gamma lactone (Ketone 32)

A heterogeneous mixture of the Reduction Product (21b) of Example 2 (5.71 g, 11.9 mmol) and potassium carbonate (1.93 g, 14.0 mmol) in methanol (200 ml) and tetrahydrofuran (20 ml) was stirred at room temperature for 3.5 hours, then was acidified (pH 3) with 1N hydrochloric acid. The acidified mixture was extracted with ethyl acetate and the combined organic extracts were washed with brine, dried (MgSO$_4$) and concentrated. Purification of the residue by column chromatography using ether as an eluent afforded 1.79 g (50%) of the above titled Ketone (32) as a viscous oil.

EXAMPLE 4

2-[3 alpha,5 alpha-dihydroxy-2-beta-(3-amino-4-phenoxybut-1-yl)cyclopent-1 alpha-yl]acetic acid, gamma-lactone (Amine 43)

To a solution of the Ketone (32) of Example 3 (1.5 g, 5.2 mmol) and ammonium acetate (4.0 g, 52.0 mmol) in methanol was added dropwise over 1.5 hours a solution of sodium cyanoborohydride (840 mg, 13.3 mmol) in methanol (25 ml). The solution was then concentrated and the residue suspended in water. The aqueous mixture was acidified (pH 2.5) with 1N hydrochloric acid and extracted with ethyl acetate. The aqueous layer was then basified (pH 10) with 1N sodium hydroxide and extracted with ethyl acetate. The combined basic extracts were washed with brine, dried (Na$_2$SO$_4$) and concentrated to give 1.06 g (66.7%) of the above titled Amine (43) as a viscous oil which was used without purification.

EXAMPLE 5

2-[3 alpha,5 alpha-dihydroxy-2 beta-(3-methanesulfonamido-4-phenoxybut-1-yl)cyclopent-1 alpha-yl]acetic acid, gamma-lactone (Sulfonylamine 54)

To a solution, cooled to −78° C. of the Amine (43) of Example 4 (1.06 g, 3.47 mmol) in methylene chloride (20 ml) was added dropwise methanesulfonyl chloride (400 mg, 3.50 mmol). The solution was stirred in the cold for 30 minutes then at room temperature for 1.5 hours. The solution was washed with brine, dried (MgSO$_4$) and concentrated. Purification of the residue by column chromatography using mixtures of ethyl acetate in benzene as eluents provided 400 mg (30%) of the above titled Sulfonylamine (54) as a viscous oil.

EXAMPLE 6

2-[5 alpha-hydroxy-3 alpha-(tetrahydropyran-2-yloxy)-2 beta-(3-methanesulfonamido-4-phenoxybut-1-yl)-cyclopent-1 alpha-yl]acetic acid, gamma lactone (Lactone 65)

A solution of Sulfonylamine (54) of Example 5 (400 mg, 1.04 mmol), dihydropyran (170 mg) and p-toluenesulfonic acid (trace) in methylene chloride was stirred at room temperature for 20 minutes, then was diluted with diethyl ether (200 ml). The organic solution was washed with saturated sodium bicarbonate and brine, dried (MgSO$_4$) and concentrated to give 486 mg (100%) of the above titled Lactone (65) as a viscous oil which was used without purification.

EXAMPLE 7

2-[5 alpha-hydroxy-3 alpha-(tetrahydropyran-2-yloxy)-2 beta-(3-methanesulfonamido-4-phenoxybut-1-yl)-cyclopent-1 alpha-yl]acetaldehyde, gamma hemiacetal (Hemiacetal 75a)

To a solution, cooled to −78° C. of the Lactone (65) of Example 6 (486 mg, 1.04 mmol) in toluene (25 ml) was added 2.5 ml of a 20% diisobutylaluminum hydride in n-hexane. The solution was stirred in the cold for one hour, then was quenched with methanol and concentrated. The residue was partitioned between diethyl ether and a 50% sodium potassium tartrate solution. The etheral layer was further extracted with 50% sodium potassium tartrate, washed with brine, dried (Na$_2$SO$_4$) and concentrated. Purification of the residue by column chromatography using diethyl ether as eluent provided 327 mg (67%) of the above titled Hemiacetal (75a) as a viscous oil.

EXAMPLE 8

9 alpha-hydroxy-11 alpha-(tetrahydropyran-2-yloxy)-15-methanesulfonamido-16-phenoxy-cis-5-omega-tetranorprostenoic acid (Wittig Product 85b)

To a solution of (4-carbohydroxy-n-butyl)triphenylphosphonium bromide (Wittig Reagent) (917 mg, 2.07 mmol) in 10 ml of dimethylsulfoxide (DMSO) was added 20 ml of a 2.0 m solution of sodium methylsulfonylmethide in DMSO. To this red ylide solution was added a solution of the Hemiacetal (75a) of Example 7 (327 mg, 0.69 mmol) in 10 ml of DMSO. The reaction mixture was stirred for 64 hours, then was poured onto a mixture of water and diethyl ether. The aqueous layer was acidified to pH 2 with 6N hydrochloric acid and extracted with ethyl acetate. The combined organic extracts were washed with brine, dried (Na$_2$SO$_4$) and concentrated. Purification of the residue by column chromatography gave 78 mg (20%) of the above titled Wittig Product (85b) as a viscous oil.

EXAMPLE 9

9-oxo-11 alpha-(tetrahydropyran-2-yloxy)-15-methanesulfonamido-16-phenoxy-cis-5-omega-tetranorprostenoic acid (Ene 96)

To a solution of the Wittig Product (85b) of Example 8 (73 mg, 0.132 mmol) in 10 ml of acetone, cooled to 0° C., was added 0.05 ml of Jones reagent (chromic acid in sulfuric acid). The reaction was stirred for 5 minutes, then was quenched with 0.05 ml of isopropanol. The reaction mixture was diluted with diethyl ether (50 ml), was washed with water and brine, dried (MgSO$_4$) and concentrated to afford 73 mg (100%) of the above titled Ene (96) as a viscous oil which was used without purification.

EXAMPLE 10

9-oxo-11 alpha-(tetrahydropyran-2-yloxy)-15-methanesulfonamido-16-phenoxyomega-tetranorprostanoic acid (Ane 107)

A heterogeneous solution of 34 mg of the Ene (96) of Example 9 and 13 mg of 5% palladium on carbon in 3 ml absolute methanol is hydrogenated (1 atm.) at 0° C. for 2 hours. The reaction mixture is filtered and evaporated to yield the above titled Ane (107).

EXAMPLE 11

9-oxo-11 alpha-hydroxy-15-methanesulfonamido-16-phenoxyomega-tetanorprostanoic acid (Derivative 118)

A solution of 34 mg of the Ane (107) of Example 10 in a 65:35 mixture of acetic acid is stirred at room temperature for 18 hours, then is concentrated. Purification of the residue using standard techniques such as column chromatography will provide the above titled Derivative (118).

EXAMPLE 12

9-oxo-11 alpha-hydroxy-15-methanesulfonamido-16-phenoxy-cis-5-omega-tetranorprostenoic acid (Derivative 128)

A solution of 73 mg (0.132 mmol) of Ene (96) of Example 9 in a 65:35 mixture of acetic acid, water (20 ml) was stirred at room temperature for 18 hours, then was concentrated. Purification of the residue by column chromatography using mixtures of ethyl acetate in chloroform as eluents provided 35 mg (56%) of the above titled Derivative (128) as a viscous, clear oil.

EXAMPLE 13

Methyl 9-oxo-11 alpha-hydroxy-15-methanesulfonamido-16-phenoxy-cis-5-omega-tetranorprostenoate (Derivative 13 ester)

A solution of 10 mg of Derivative (128) of Example 12 and ether (5 ml) is treated with diazomethane in ether (2 ml, 0.1M). After stirring for 5 min, the ether is evaporated to provide the above titled Derivative (13 ester). The analogous treatment with a solution of diphenyl sulfate in ether (2 ml, 0.1 M) will provide the phenyl ester.

SYNTHESIS OF OTHER DERIVATIVES

Using the procedures given by Examples 1 through 13 and by substituting the appropriate Coupling Reagent (CH$_3$O)$_2$POCH$_2$COCH$_2$C$_6$H$_4$X for dimethyl(2-oxo-3-phenoxypropyl)phosphate in Example 1 and the appropriate Wittig Reagent Ph$_3$P(CH$_2$)$_4$QBr wherein Q is other than CO$_2$R for (4-carbohydroxy-n-butyl)triphenyl phosphonium bromide in Example 8, the other 15-sulfonamidoprostaglandin derivatives wherein Y is OH may be synthesized.

Using the procedures given by Examples 1, 2, 4, 5, 7 through 10 and 13 and the reagent substitutions given in the above paragraph and by substituting 2-[5 alpha-hydroxy-2 beta-formylcyclopent-1 alpha-yl]acetic acid, gamma lactone for 2-[3 alpha-p-phenylbenzoyloxy-5 alpha-hydroxy-2 beta-formylcyclopent-1 alpha-yl]acetic acid, gamma lactone in Example 1, the other 15-sulfonamidoprostaglandin derivatives wherein Y is H may be synthesized.

BIOLOGICAL EVALUATION IN VITRO GUINEA PIG UTERINE STRIP

Nulliparous guinea pig females (300–400 g) which were not in estrus were sacrificed by cervical dislocation. The uteri were removed and suspended in a 2 ml tissue bath containing modified Krebs solution at 37° C. and uterine contractions were measured with a linear motion transducer (Phipps and Bird, model ST-2). Tissues were allowed to stabilize for 20–30 minutes and were then exposed to $PGE_2$ or the derivative, washed and allowed to return to baseline condition. All determinations were an average of responses for at least three individual tissues to each concentration of the derivative tested (Derivative 128). Data for this derivative were compared to those for $PGE_2$ obtained with the same tissue. Potency was estimated from concentration-response curves. An equimolar dose of Derivative (128) caused a significantly reduced response compared to $PGE_2$.

IN VIVO GUINEA PIG HISTAMINE AEROSOL TEST

Bronchodilator activity was evaluated according to the method of Van Arman, Miller and O'Malley (1961)[1] in conscious female Reed-Willet guinea pigs (200 to 250 g) fasted overnight. Derivative (128), dissolved in 90% ethanol-water, was placed in a Vaponephrine Standard Nebulizer (Vanonephrine Company, Edison, New Jersey) and sprayed for one minute under an air pressure of 6.5 lb/in$^2$ into a closed 8×8×12 inch transparent plastic container. Each animal was exposed to the Derivative or vehicle aerosol for 2 minutes, including the nebulization period. Immediately thereafter the guinea pig was placed in an identical container into which a 0.2% solution of histamine dihydrochloride had been nebulized for one minute. At the end of one minute exposure to histamine the respiratory status of the guinea pig (indicative of bronchial tone) was scored as follows: 0, normal breathing; 1, slightly deepened breathing; 2, labored breathing; 3, severely labored breathing and ataxia; 4, unconsciousness. The scores for control groups exposed to vehicle alone and test groups (8 animals per group) were summed and compared and the difference expressed as percent protection. An equimolar dose of Derivative (128) caused little bronchodilation compared to $PGE_2$.

[1] C. G. Van Arman, L. M. Miller, and M. P. O'Malley, *J. Pharmacol. Exp. Ther.*, 153, 90 (1961).

IN VIVO DOG ANTISECRETORY TEST

Gastric antisecretory activity was studied in overnight fasted, conscious Heidenhain pouch dogs (F) using pentagastrin to stimulate acid output. Pentagastrin was administered as a continuous infusion into a superficial leg vein at doses earlier determined to stimulate near maximal acid output from the gastric pouch. All dogs in this study weighed 8–12.5 kg. Gastric juice was collected at 30 minute intervals following the start of a pentagastrin infusion. A total of ten collections were made for each dog during an experiment. Derivative (128) or $PGE_2$ was administered orally or intravenously after the third gastric juice collection. All sample volumes were recorded and acid concentration was determined by titrating sample aliquots (1.0 ml) to pH 7.4 with 0.1 N NaOH using a pH meter (Radiometer) and autoburette. Results were determined as a percent decrease in the pH of the gastric effluent with respect to time (potency×duration). An i.v. dose of 5 microgram/kg of Derivative (128) caused a 36% inhibition of stimulated acid output.

It is claimed:
1. A 15-sulfonamidoprostaglandin derivative of the formula:

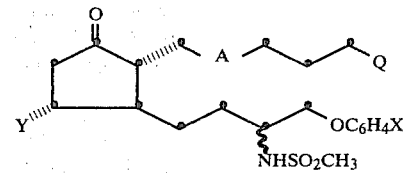

or the pharmacologically acceptable salt thereof, wherein:
Q is —$CO_2H$, —$CO_2R$, tetrazol-5-yl, —$CONHSO_2R$ or —CONHCOR;
A is ethylene or cis-vinylene;
Y is H or OH;
X is H, F, Cl, Br, $OCH_3$, $CF_3$ or $CH_3$; and
R is alkyl of 1 to 4 carbons or phenyl.
2. The derivative of claim 1 wherein Q is $CO_2H$, A is cis-vinylene, Y is OH and X is H.
3. The derivative of claim 1 wherein Q is $CONHSO_2CH_3$, A is cis-vinylene, Y is OH and X is H.
4. The derivative of claim 1 wherein Q is $CONHSO_2CH_3$, A is cis-vinylene, Y is H and X is H.
5. The derivative of claim 1 wherein Q is tetrazol-5-yl, A is cis-vinylene, Y is OH and X is H.
6. A pharmaceutical preparation for treating peptic ulcers, which comprises:
a pharmaceutical carrier and
an efficacious amount of a derivative of claim 1.
7. A method of treating peptic ulcers, which comprises:
administering an efficacious amount of a derivative of claim 1 to a patient in need of such treatment.

* * * * *